United States Patent

Franc et al.

[11] Patent Number: 5,804,192
[45] Date of Patent: Sep. 8, 1998

[54] PROCESS FOR OBTAINING PROCYANIDOL OLIGOMERS FROM PLANTS BY EXTRACTIONS

[75] Inventors: Bruno Franc, Saze; Christian Hoff, St Laurent des Arbres, both of France

[73] Assignee: Sanofi, Paris, France

[21] Appl. No.: 539,463

[22] Filed: Oct. 5, 1995

[30] Foreign Application Priority Data

Oct. 11, 1994 [FR] France .................................. 94 12126

[51] Int. Cl.⁶ .......................... A01N 65/00; A61K 35/78; A61K 39/385; B01D 61/00
[52] U.S. Cl. ........................................ 424/195.1; 210/650
[58] Field of Search .......................... 424/195.1; 210/650

[56] References Cited

FOREIGN PATENT DOCUMENTS

| 0348781 | 1/1990 | European Pat. Off. . |
| 1427100 | 12/1965 | France . |
| 2092743 | 1/1972 | France . |
| 2218109 | 9/1974 | France . |
| 2372823 | 6/1978 | France . |
| 626359 | 12/1978 | Switzerland . |
| 884184 | 12/1961 | United Kingdom . |
| 1541469 | 12/1976 | United Kingdom . |

*Primary Examiner*—Marian C. Knode
*Assistant Examiner*—Ali R. Salimi
*Attorney, Agent, or Firm*—Jacobson, Price, Holman & Stern, PLLC

[57] ABSTRACT

The invention relates to a process for obtaining procyanidol oligomers according to which:

an appropriate plant is treated by means of an extractive mixture composed of water, of a water-miscible organic solvent capable of dissolving the procyanidol oligomers and of sodium chloride, the crude mixture of procyanidol oligomers obtained is purified by removal of the extractive mixture and extraction of the residue, the extractive mixture optionally being recycled in the stage of treatment of the plant, the procyanidol oligomers are recovered in a pure form by precipitation.

10 Claims, No Drawings

PROCESS FOR OBTAINING PROCYANIDOL OLIGOMERS FROM PLANTS BY EXTRACTIONS

The present invention relates generally to a new process for obtaining flavanol or procyanidol substances present in plants.

More particularly, the invention relates to a method of extraction, from plants, which makes it possible, on an industrial scale, to extract all the procyanidol oligomers which they contain.

The procyanidol oligomers can be defined as representing relatively complex mixtures of flavone substances composed essentially of catechin derivatives and of polymers from the condensation of 2 to 5 flavanol molecules.

These mixtures constitute homogeneous substances which have notable pharmacological properties making them particularly useful in the treatment of various diseases, particularly disorders of the circulatory system.

For example, procyanidol oligomers consisting of a purified grapeseed extract are currently marketed for their properties in protecting veins.

This extract corresponds to generally accepted standards derived from precise analytical specifications defining a balance between monomers, oligomers and tannins.

There are already many known processes for extracting procyanidol oligomers, or similar substances, present in plants, in particular in grapeseed, which contains significant amounts thereof and which for this reason constitutes one of the most suitable potential sources for industrial use.

Mention may be made, to this end, of the processes described in Patents FR 968,589, 1,036,922 and 1,427,100. However, none of these processes makes it possible to obtain all the procyanidol oligomers present in the plants.

Mention may additionally be made of Patent GB 884,184 which relates to a process which makes it possible, when applied to a plant, to collect all the procyanidol oligomers present in this plant.

This process is characterized in that the chosen plant is extracted with water, at high temperature in the absence of oxygen or at low temperature or with organic solvents, such as an alcohol or acetone, or with a mixture of the latter with water, the impurities which are also extracted being precipitated by adding to the reaction mixture an aqueous solution containing 250 g/l of sodium chloride. The filtrate is then extracted with ethyl acetate and the solvent is removed to give the desired procyanidol oligomers.

This process, while making it possible to extract all the oligomers without denaturing them, cannot be validly used on an industrial scale, firstly because of the low yield which it provides and then because it requires the use of a very large amount of sodium chloride, i.e. 1 to 1.5 tonnes per tonne of starting materials.

The use of such a process industrially would cause not only difficulties in handling and in storage but also problems of removal due to the sodium chloride.

Likewise, Patent FR 2,372,823 describes a process for the extraction of procyanidol oligomers which is based on the following stages:
extraction of the plant with an acetone/water mixture containing from 3 to 4 volumes of acetone per volume of water,
removal of the acetone by evaporation and filtration of the impurities,
extraction of the aqueous filtrate with ethyl acetate,
removal of the solvent, taking up the residue again in water and drying under vacuum,
precipitation of the impurities by addition of a saturated aqueous sodium chloride solution and filtration,
extraction of the aqueous filtrate with ethyl acetate and partial evaporation of the solvent,
precipitation of the procyanidol oligomers by addition of chloroform and then drying.

However, this process does not overcome the disadvantages displayed by the process of Patent GB 884,184 since it also involves aqueous solutions highly concentrates in sodium chloride which, if left in the environment, are capable of causing serious harm due to pollution.

As regards the yields afforded by this process, these prove to be extremely restricted, since they are of the order of 0.6%.

It will moreover be mentioned that the prior processes calling for water/acetone mixtures with a high acetone content cause the concomitant extraction of resins which it is necessary to separate in a special stage.

The development of a process for obtaining procyanidol oligomers which is capable of being used on an industrial scale and which makes it possible to overcome the above disadvantages while providing a product conforming to the generally accepted standards and with a satisfactory yield remains of major interest.

It has now been discovered that it is possible to obtain all the procyanidol oligomers present in the plants according to an industrial extraction process capable of overcoming the disadvantages of the prior processes while providing a higher yield of analytically conforming oligomers.

According to the invention, the procyanidol oligomers are obtained by:
treatment of an appropriate plant by means of an extractive mixture, namely a mixture composed of water, of a water-miscible organic solvent capable of dissolving the procyanidol oligomers and of sodium chloride,
purification of the crude mixture of procyanidol oligomers obtained by removal of the extractive mixture and extraction of the residue,
recovery of the procyanidol oligomers by precipitation.

According to a preferred implementation of the above process, the extractive mixture, that is to say the water-miscible organic solvent, on the one hand, and the aqueous phase containing sodium chloride, on the other hand, is recycled, after its removal, into the stage of treatment of the plant.

The process of the invention is consequently characterized by a stage of extraction of the plant, carried out with a mixture containing 3 components.

This extraction stage is generally carried out with heating, that is to say at a temperature of the order of 50° to 70° C., preferably at a temperature of 55° to 60° C., in order to obtain, with acceptable kinetics, correct and through extraction of the plant, for example of grapeseeds.

To this end, use is made of an extractive mixture consisting of water and of a water-miscible organic solvent capable of dissolving the procyanidol oligomers, to which sodium chloride has been added. This water-miscible organic solvent, generally a ketone compound which has $C_1$–$C_4$ substituents, such as, for example, acetone, methyl ethyl ketone or methyl isopropyl ketone, is used in a proportion of 25 to 50% of the weight of the water, preferably of 30 to 35%.

A water/acetone/sodium chloride mixture is usually preferred as extractive mixture.

As regards the sodium chloride, this is incorporated in the water/water-miscible organic solvent mixture in a proportion of 5 to 35% of the weight of the water, depending on the composition of the mixture of procyanidol oligomers to be obtained.

The sodium chloride concentration in fact plays an important role in the qualitative composition of the procyanidol oligomers extracted.

A large variation in the distribution of monomers, oligomers and tannins as a function of the salt concentration has in fact been noticed. For example, a sodium chloride concentration of 360 g/l of water makes it possible to obtain an extract containing 41% of monomers but free of tannins, whereas a concentration of 180 g/l of water provides an extract containing 30% of monomers with a better-balanced oligomer/tannin ratio.

In order to obtain a procyanidol oligomer extract conforming to the generally accepted standards which were mentioned above, use is preferably made of sodium chloride at a concentration of 15 to 20% of the weight of the water, for example at the concentration of 18% of the weight of the water.

According to a specific implementation of the process of the invention, the procyanidol oligomers are obtained by application of the sequence of stages below:

1) treatment of the plant, for example powdered grapeseeds, with an extractive mixture composed of water, of a water-miscible organic solvent capable of dissolving the procyanidol oligomers, preferably acetone, and of sodium chloride,
2) removal of the water-miscible organic solvent by distillation and recycling of this distillate into the stage of treatment of the plant,
3) addition to the residue of a water-immiscible organic solvent capable of dissolving the procyanidol oligomers present in this residue, such as, for example, ethyl acetate,
4) filtration of the suspension obtained and extraction of the filtrate with the water-immiscible organic solvent used in the preceding stage, for example ethyl acetate, or with any other organic solvent which may be suitable for this purpose, in order to obtain an organic extract, and recycling of the aqueous phase containing sodium chloride into the stage of extraction of the plant,
5) concentration by partial evaporation of the solvent from the above organic extract, dehydration and concentration by a further partial evaporation of the solvent,
6) precipitation and drying of the procyanidol oligomers, the precipitation being carried out by adding to the concentrated organic solution an organic solvent which does not dissolve the oligomers, such as, for example, dichloromethane or preferentially dichloroethane.

Compared with the prior art, the process of the invention has undeniable advantages, which may be summarized as follows:

elimination of a stage for filtering out impurities (resins), after the stage of extraction of the plant use of a reduced volume of water-miscible organic solvent, such as acetone replacement of chloroform by an organic agent which is markedly less toxic, such as dichloroethane. In addition to this characteristic, dichloroethane allows a more satisfactory removal of the water-immiscible organic solvent, for example ethyl acetate.

Furthermore, the process of the invention, in its preferential aspect, makes it possible to recycle the water-miscible organic compound, such as acetone, and to avoid discharging the aqueous phase containing sodium chloride.

In addition, this salted aqueous phase can be recycled a number of times without unfavourable repercussions on the quality of the procyanidol oligomers obtained. The process thus designed makes it possible to obtain the analytically conforming oligomers in question in a yield of 1.5 to 2.5%, that is to say 3 to 4 times higher than the yields afforded by the state of the art.

The following non-limiting example illustrates the process of the invention.

EXAMPLE

Continuous process for obtaining procyanidol oligomers

An extractive mixture is first prepared, with the following composition:

| Deionized water: | 1650 l |
| Sodium chloride: | 300 kg |
| Acetone: | 550 l |

Finely ground grapeseeds are then extracted for 2 hours at a temperature of 55° to 60° C., using a screw conveyor extractor, at the rate of a grapeseeds throughput of 20 kg/h and of a throughput of 100 l/h of the extractive mixture which moves countercurrentwise.

On leaving the extractor, before clarification on a centrifuge, the miscella is cooled to 20° C. using a heat exchanger, acetone is stripped therefrom by distillation under reduced pressure at a temperature of 45° C. and the distillate is recycled as is into the stage of extraction of the grapeseeds.

1 kg of cellulose foam, as filter aid, and 40 l of ethyl acetate, as flocculating agent for the resins, are then added to the residue obtained. These amounts are specific for 5 hours of operation.

The suspension is filtered on a centrifuge rendered inert by addition of a cellulose precoat, the filtrate is extracted with 5×45 l ethyl acetate fractions and the exhaustively extracted aqueous phase is recycled into the stage of extraction of the grapeseeds after topping in order to remove entrained ethyl acetate.

The ethyl acetate extract is concentrated under reduced pressure at a temperature below 40° C. to a residual volume of 125 l. The residue obtained is dehydrated by stirring with 8 kg of sodium sulphate, the suspension is filtered and the filtrate is then concentrated under the same conditions as above to a residual volume of 9 l.

After cooling to 20° C., the procyanidol oligomers are then precipitated by addition of 45 l of dichloroethane.

The very fine solid obtained is then filtered under nitrogen on an enclosed filter drier and is rinsed with 6 l of dichloroethane. In this way, from 1.5 kg to 2.5 kg of procyanidol oligomers are obtained per 100 kg of grapeseeds (yield: 1.5 to 2.5%).

The crude product obtained is next rid of its residual solvents by dissolving in water and is then sprayed.

We claim:

1. A process for obtaining procyanidol oligomers, by extraction from plants containing them comprising the steps of:
   a) treating a plant with an extractive mixture comprising water, water-miscible organic solvent capable of dissolving the procyanidol oligomers, in a proportion of 25 to 50% of the weight of the water, and sodium chloride, in a proportion of 15 to 20% of the weight of the water to obtain a crude mixture of procyanidol oligomers,
   b) concentrating the crude mixture of step (a),
   c) purifying the concentrated crude mixture of step (b) by removing the extractive mixture and extracting the residue,
   d) recovering the procyanidol oligomers in a pure form by precipitation, and e) drying said precipitation of procyanidol oligomers from step (d).

2. The process according to claim 1, wherein the extractive mixture is recycled into the stage of treatment of the plant.

3. The process according to claim 1, wherein:

the plant is treated with the extractive mixture comprising water, the solvent capable of dissolving the procyanidol oligomers, in a proportion of 25 to 50% of the weight of the water, and sodium chloride, in a proportion of 15 to 20% of the weight of the water, the water-miscible organic solvent is removed by distillation and the distillate is recycled into the stage of treatment of the plant said distillation producing a residue, a water-immiscible organic solvent capable of dissolving the procyanidol oligomers present in the residue is added to the residue produced by the organic solvent distillation, the crude mixture obtained in step (a) is filtered and the filtrate is extracted with the water-immiscible organic solvent or with any other organic solvent, in order to obtain an organic extract, and the aqueous phase containing sodium chloride is recycled into the stage of treatment of the plant, the concentration is carried out by partial evaporation of the solvent from the above organic extract, dehydration is carried out and concentration is again carried out by partial evaporation of the solvent, the procyanidol oligomers are precipitated by adding to the concentrated organic solution an organic solvent which does not dissolve the procyanidol oligomers.

4. The process according to claim 1, wherein the plant consists of grapeseeds.

5. The process according to claim 1, wherein the treatment of the plant takes place at a temperature of 50° C. to 70° C.

6. The process according to claim 1, wherein the water-miscible organic solvent is used in a proportion of 30 to 35% of the weight of the water.

7. The process according to claim 1, wherein the water-miscible solvent is a ketone compound which has $C_1$–$C_4$ substituents.

8. The process according to claim 7, wherein the said ketone compound is acetone.

9. The process according to claim 3, wherein the water-immiscible organic solvent is ethyl acetate.

10. The process according to claim 3, wherein precipitation takes place by addition of dichloromethane or dichloroethane to the concentrated organic solution.

* * * * *